United States Patent [19]

Roberts

[11] Patent Number: 4,619,649
[45] Date of Patent: Oct. 28, 1986

[54] DISPOSABLE TODDLER TRAINING PANTY

[76] Inventor: Joan Roberts, 2337 Edgebrook Dr., Modesto, Calif. 96351

[21] Appl. No.: 605,641

[22] Filed: Apr. 30, 1984

[51] Int. Cl.$^4$ .............................................. A61F 13/16
[52] U.S. Cl. ................................. 604/396; 604/385 A
[58] Field of Search .............. 604/389, 390, 396, 394, 604/385; 2/403, 73, 74, DIG. 7, 275; 383/73

[56] References Cited

U.S. PATENT DOCUMENTS

| | | | |
|---|---|---|---|
| 2,678,648 | 5/1954 | DeWoskin | 604/396 |
| 2,724,120 | 11/1955 | Biern | 2/74 |
| 2,834,347 | 5/1958 | Connally | 604/389 |
| 2,934,255 | 4/1960 | McDuffie | 383/79 |
| 2,944,550 | 7/1960 | Magid . | |
| 3,035,576 | 5/1962 | Collier | 604/396 |
| 3,175,753 | 4/1965 | Civitello | 383/79 |
| 3,554,195 | 1/1971 | Murdoch . | |
| 3,599,638 | 8/1971 | Rickard | 604/396 |
| 3,599,640 | 7/1971 | Larson | 604/394 |
| 3,631,686 | 10/1971 | DeWoskin | 604/396 |
| 3,749,095 | 7/1973 | Toyama | 604/396 |
| 3,756,878 | 9/1973 | Willot . | |
| 3,828,785 | 7/1974 | Gamm | 604/394 |
| 3,916,447 | 11/1975 | Thompson | 2/DIG. 7 |
| 3,931,666 | 1/1976 | Karami | 604/390 |
| 4,018,226 | 4/1977 | Korgemets | 604/392 |
| 4,122,552 | 10/1978 | Tedford | 604/390 |
| 4,145,763 | 3/1979 | Abrams et al. | 2/403 |
| 4,205,679 | 6/1980 | Repke | 604/394 |

FOREIGN PATENT DOCUMENTS 0159262  5/1935  Fed. Rep. of Germany ... 128/290 R Primary Examiner—C. Fred Rosenbaum
Assistant Examiner—Karen L. Kaechele
Attorney, Agent, or Firm—Leonard Bloom

[57] ABSTRACT

A disposable toddler training panty having a thin plastic outer layer provided on an inner surface with a comfortable soft inner lining, the panty having an elastic waistband and legbands, a thin absorbent padded crotch area, and separable side seams from the waistband to the legband on both sides to allow for easy removal of the toddler panty in the event of the soiling of same.

10 Claims, 5 Drawing Figures

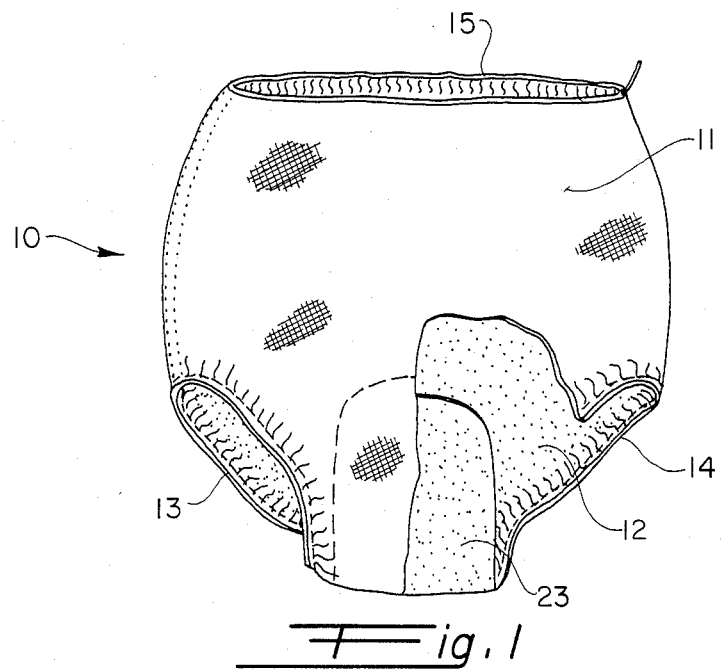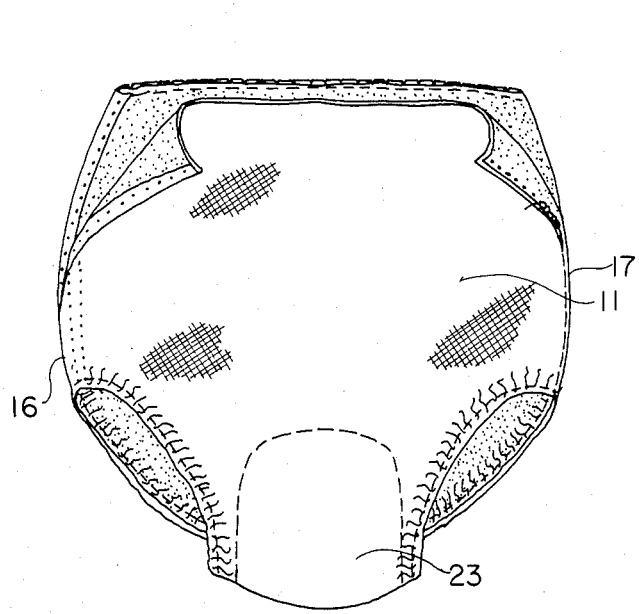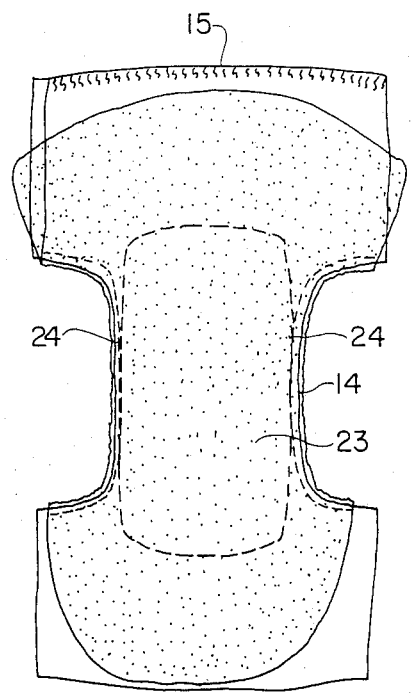

DISPOSABLE TODDLER TRAINING PANTY

BACKGROUND OF THE INVENTION

The present invention relates generally to the field of disposable diapers for infants and small children and more specifically to a disposable toddler training panty to be used during the period when a small child is being toilet trained.

During the difficult period when a child is being toilet trained, there are a number of transitions which must be accomplished. Most particularly, during the waking hours, a child must adapt to a new form of undergarment, discarding the conventional diaper and wearing some sort of a less bulky panty in its place. It is well known in the prior art to substitute a cloth training pant for a diaper during the transitional period of toilet training. During this period the child begins to recognize the difference in the garments and the different behavior modes he or she should adopt as a result thereof. However, during this transitional period the child often soils the training pants as the learning process progresses. This presents every working or nonworking mother with the highly undesirable task of rinsing out the cloth training pants which have been substituted for the disposal diaper employed prior to toilet training.

Applicant has operated a family daycare center for twenty-five years and has performed the unenviable task of toilet training a great number of children. Although it is an essential part of the toilet training process to acclimate the child to a different form of undergarment, such as training pants, it is not essential that the training pants be of the cloth or nondisposable variety. In fact, there is a strong felt yet unfulfilled need for a disposable toddler training panty which is which is thin enough and distinct enough from a diaper to alert the child of the new form of garment being used during the toliet training process so that the child becomes aware of an expected change in his or her behavior.

The present invention is designed to have the convenience of the disposable diaper while still being light enough and distinct enough from a diaper so that the child is aware of the difference. Thus, the instant invention is intended to have the same function as a regular cloth toddler training panty, with the advantage of not having to be rinsed out by hand after being soiled. After the transition period, the child will readily adapt to a child's panty or shorts made from cloth.

Normally toddler training pants are worn by placing the child's feet in the leg holes and sliding the training pants up into the proper position, and removal is accomplished by the reverse process. However, if the training pants are soiled then removal becomes an offensive task. The disposable toddler training pants according to the instant application overcome this problem by providing side portions with a perforate seam or a chain stitched seam along each side thereof, so that the seams can be readily split apart from the waistband to the legband on both sides thereby providing for easy removal of the training panties.

The following citations represent the prior art of which applicant is aware that may be germane to the patent process:
U.S. Pat. No. 2,944,550, Magid;
U.S. Pat. No. 3,554,195, Murdoch;
U.S. Pat. No. 3,599,638, Rickard;
U.S. Pat. No. 3,756,878, Willot.

The patent to Magid is of interest since it teaches the use of a thermoplastic panty having separable side portions to accommodate a front removal therefrom. The separable side seams 28 provided in Magid are heat sealed and designed to be detachably rejoined for further use. The device according to the instant application is easily distinquished in that the training pants are designed to be completely disposable after one use and are provided along interior portions with a soft inner lining in conjunction with an absorbent padded area. Furthermore, the side seams associated with the instant invention are simply a perforate or a stitched area and designed to be stripped to an open position quite readily and thereafter removed for disposal.

The remaining citations further delineate the state of the art, however none of the citations taken singly or in any conceivable combination would appear to anticipate nor render obvious the invention as disclosed herein.

SUMMARY AND OBJECTS OF THE INVENTION

Accordingly, it is a primary object of the present invention to provide a disposable toddler training panty having a thin plastic outer surface provided with elastic legbands and waistband to accommodate toddlers of different sizes, and further provided on the inner surface thereof with a soft lining to lie next to the skin of the toddler to insure for the comfort of the child. The instant panty is further provided with a thin absorbent pad interposed between the outer plastic layer and the inner soft layer in the crotch area of the panty to absorb any wetness. In order for quick removal in the case of the panty becoming soiled, the side seams from the waistband to the legband are quickly separable due to perforations or a chain stitching so that the toddler training panty may be quickly removed and disposed of. The disposable toddler taining panty described herein is designed to have the weight, feel, and appearance of a cloth toddler panty so that the toilet training process is augmented by the garment in that the child recognizes the distinction between a diaper and the toddler training panty so that a different mode of behavior is emphasized when the disposable toddler panty is worn which emulates the situation when a cloth toddler panty is worn during the transition period of toilet training.

It is a further object of the present invention to provide a novel disposable toddler training panty which has a very flexible absorbent pad in the crotch area so that the stiffness and bulkiness of a regular diaper is eliminated thereby alerting the child to a difference in feeling associated with the transitional undergarment.

It is a still further object of the present invention to provide a novel disposable toddler training panty which has provided the legbands and waistband with elasticity to accommodate toddlers of various sizes.

It is another object of the present invention to provide a novel disposable toddler training panty which can be easily removed from the toddler by separating the seams at the side portions which can be accomplished with one hand while holding the toddler with the other.

It is still another object of the present invention to provide a novel disposable toddler training panty which is simple in construction, inexpensive to manufacture, and lends itself well to mass production techniques.

It is a still further object of the present invention to provide a novel disposable toddler training panty which eliminates the traditional use of the plastic rubber panties over a pair of cloth training panties to avoid the wetting of outer garments, thereby reducing costs and bother.

These and other objects are accomplished by the provision of a disposable toddler training panty having a plastic exterior surface, a soft comfortable interior surface with a this absorbent padded area in the crotch portion, elasticity at the legbands and waistband, and separable side seams from the legband to the waistband to permit easy removal of the panty in case of the soiling of same.

BRIEF DESCRIPTION OF THE DRAWINGS

FIG. 1 is a front partial fractional view of the toddler panty.

FIG. 2 is a front view showing the separable side seams.

FIG. 3 is a top view of a toddler panty after having been separated on side seams and laid out flat.

DESCRIPTION OF THE PREFERRED EMBODIMENT

Figure 4:
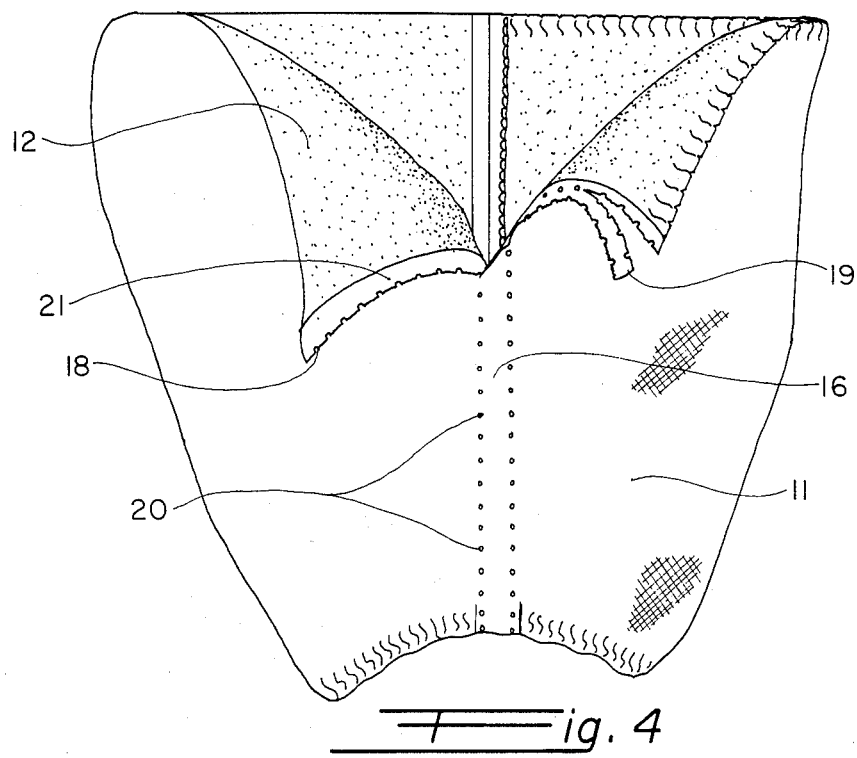
FIG. 4 is a side view of the toddler panty showing a partially separated perforate side seam.

Referring now to the drawings in detail wherein like reference numerals represent like parts throughout the several figures, reference numeral 10 refers generally to the toddler panty. The panty has a thin plastic water resistant exterior surface 11, which is provided on an interior surface with a soft lining 12 which provides a comfortable cushion between the toddler's skin and the training panty. The lining 12 may be fabricated from a cotton or paperlike substance or any appropriate material that provides the necessary zone of comfort. The lining layer 12 may be affixed to the outer layer 11 by adhesive along peripheral zones thereof. For example, the inner lining 12 may be affixed to the outer layer 11 along the periphery of legband area 13 and legband area 14 and along the periphery of waistband area 15. The fusion of the inner lining 12 to the outer layer 11 at the above described points allows a degree of independent flexible movement for the inner layer 12 which reduces the possibility of any chaffing to the skin of the child.

As shown in FIG. 2, the side seams 16 and 17 are separable to provide a means for quick and easy removal and disposal of the toddler panty. In a preferred embodiment, the side seams may be either perforate, as is side seam 16, or be joined by a chain stitch, as is side seam 17. Referring now to FIG. 4, the perforate side seam 16 is formed by overlapping and using a side edge portion 19 of the outer lining 11 with similar edge portion 18 then providing perforations 20 to allow separation of the fused area by tearing same. The inner lining 12 is absent from the overlap zone 21 on both edge portions 18 and 19 to allow for easy fusion and perforation of the perforate side seam 16. The separation of the perforate side seam 16 is accomplished by tearing same which separates the side seam 16 from the waist 15 to the legband 13 which separates the front of the toddler panty from the back of the toddler panty except through the crotch area. The perforate side seam 16 may be provided on both sides of the toddler panty, or in the alternative, a chain stitch side seam 17 may be provided on both sides of the panty.

Figure 5:
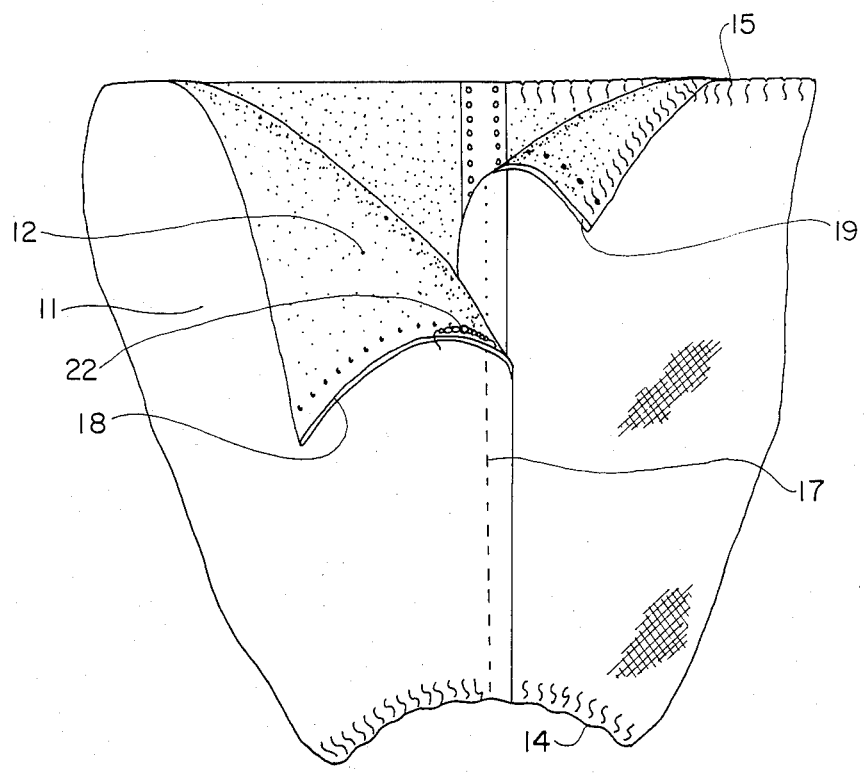
FIG. 5 is a side view of a toddler panty showing a partially separated side seam of the chain stitched species.

Referring now to FIG. 5, the inner lining 12 may be extended through the overlap zone to the edge 18 and edge 19 of the outer layer 12 and with the front overlapping the back then a chain stitch 22 may be employed to form the side seam 17 joining the front and back portions from the legband 14 to the waistband 15. Separation of the seam 17 is accomplished by grabbing the chain stitch 12 and pulling same which disassociates edges 18 and 19 allowing the front and back portions of the panty to separate from the waistband 15 to the legband 14.

Referring now to FIG. 3, a zone through the crotch area is provided with an absorbent padded layer 23, which layer is interposed between the inner lining 12 and fused to the outer layer 11. The pad 23 is constructed from any appropriate absorbent material such as cotton or a fiberous paper material, and is provided to be an absorbent pad to absorb any moisture which may be discharged during the transitional period of toddler training. The pad 23 should be of minimal thickness to accomplish the absorbancy task while providing the flexibility to allow the child to recognize the difference between a diaper and the toddler training panty so that association of the new undergarment is connected with a new expected mode of behavior.

The legbands 14 and 15 are gathered and provided along an inner peripheral portion with elastic material 24 represented by the dotted line in FIG. 3. This allows the legband to accommodate legs of various sizes so that one size of toddler training panty fits all.

Similarly, the back half of the waistband 15 is provided with an elastic member 24 and gathered so that the panty may accommodate toddlers of various girth, while the front portion of the waistband remains ungathered to maintain a flat comfortable fit.

In use and operation, the disposable toddler training panty is employed in exactly the same manner as a cloth toddler training panty which is used in the transitional period from a diaper undergarment to a normal child's panty. However, the disposable toddler training panty of the instant invention may be easily separated along side seams thereof for quick removal from the child in the event of soiling during the toddler training period so that one attending the child is relieved from the unpleasant task of rinsing and washing the cloth toddler panty. The instant toddler panty may be readily disposed of and replaced with new fresh one. The construction and nature of the disposable toddler panty 10 is very similar to that of a cloth toddler panty so that the child recognizes the difference in the transitional undergarment and can easily adapt the new mode of behavior expected while wearing the transitional garment.

It should be noted that numerous structural modifications and changes may be resorted to without parting from the spirit of the invention.

What is claimed is:

1. A disposable toddler training panty, comprising a front panel having a non-permeable outer layer and a soft inner layer,
   a rear panel having a non-permeable outer layer and a soft inner layer,
   said front and rear panels being contiguous through a crotch area,
   a thin absorbent pad interposed between said outer and said inner layers through said crotch area, and separable side seams joining said front and rear panels along side edge portions thereof, wherein said separable side seams further comprise, overlapping an edge portion of said front panel with a similar edge portion of said rear panel with only said outer layers in contact and bonding same, said same being provided with a plurality of perforations along the length thereof providing a means of seam separation by tearing same, and whereby separating both said side seams allows for easy removal of said toddler training panty from a toddler.

2. The device as recited in claim 1, wherein said seam is bonded by means of a heat seal.

3. The device as recited in claim 1, wherein said seal is bonded by adhesive means.

4. The device as recited in claim 1, whereby said rear panel further comprises, an elastic expansion and contraction medium disposed along a top edge portion of said rear panel to provide an expandable waistband to adjust to toddlers of various girth.

5. The device as recited in claim 1, wherein said crotch area defined by said front and rear panels further comprises, elastic expansion and contraction medium disposed along outward side edge portions of said crotch area, said edge portions gathered to form adjustable leg receiving passages on opposed bottom corners of said toddler training panty to accommodate toddlers of various leg girth.

6. The device as recited in claim 1, wherein said separable side seams extend substantially vertically from said waistband to said leg receiving passages, whereby separation of said seams interrupts said waistband and said leg passages allowing said toddler training panty to fall away from a toddler without any special positioning of the child.

7. The device as recited in claim 1, wherein said outer layer of said front and rear panels further comprises, a thin sheet of plastic material which is substantially non-permeable to moisture to prevent moisture from migrating from within said toddler training panty to the outside of same.

8. The device as recited in claim 1, wherein said inner layer of said front and rear panels further comprises, a soft, thin cotton-like material substantially the same size and configuration as said outer layer and affixed to same along all peripheral edge portions thereof so that central zones of said inner layer move substantially independently of said outer layer to prevent chafing of a toddler by said inner layer.

9. The device as recited in claim 1, wherein said absorbent pad further comprises, a thin cotton-like pad interposed between said outer and inner layers and affixed to said outer layer longitudinally substantially throughout said crotch zone, said pad placed to absorb any moisture emitted by a toddler wearing said toddler training panty.

10. A disposable toddler training panty, comprising a front panel having a non-permeable outer layer and a soft inner layer, a rear panel having a non-permeable outer layer and a soft inner layer, said front and rear panels being contiguous through a crotch area, a thin absorbent pad interposed between said outer and said inner layers through said crotch area, and separable side seams joining said front and rear panels along side edge portions thereof, wherein said separable side seams further comprise, an overlapping edge portion of said front panel with a similar edge portion of said rear panel with only said outer layers in contact and bonding same, said seam being provided with a plurality of perforations along the length thereof providing a means of seam separation by tearing same, and whereby separating both said side seams allows for easy removal of said toddler training panty from a toddler, whereby said rear panel further comprises, an elastic expansion and contraction medium disposed along a top edge portion of said rear panel to provide an expandable waistband to adjust to toddlers of various girth, wherein said crotch area defined by said front and rear panels further comprises, elastic expansion and contraction medium disposed along outward side edge portions of said crotch area, said edge portions gathered to form adjustable leg receiving passages on opposed bottom corners of said toddler training panty to accommodate toddlers of various leg girth, wherein said separable side seams extend substantially vertically from said waistband to said leg receiving passages, whereby separation of said seams interrupts said waist band and said leg passages allowing said toddler training panty to fall away from a toddler without any special positioning of the child, wherein said outer layer of said front and rear panels further comprises, a thin sheet of plastic material which is substantially non-permeable to moisture to prevent moisture from migrating from within said toddler training panty to the outside of same, wherein said inner layer of said front and rear panels further comprises, a soft, thin cotton-like material substantially the same size and configuration as said outer layer and affixed to same along all peripheral edge portions thereof so that central zones of said inner layer move substantially independently of said outer layer to prevent chafing of a toddler by said inner layer, wherein said absorbent pad further comprises, a thin cotton-like pad interposed between said outer and inner layers and affixed to said outer layer longitudinally substantially throughout said crotch zone, said pad placed to absorb any moisture emitted by a toddler wearing said toddler training panty.

* * * * *